United States Patent
Dassau et al.

(10) Patent No.: US 10,878,964 B2
(45) Date of Patent: Dec. 29, 2020

(54) PREDICTIVE CONTROL MODEL FOR THE ARTIFICIAL PANCREAS USING PAST PREDICTIONS

(71) Applicants: PRESIDENT AND FELLOWS OF HARVARD COLLEGE, Cambridge, MA (US); THE REGENTS OF THE UNIVERSITY OF CALIFORNIA, Oakland, CA (US)

(72) Inventors: Eyal Dassau, Acton, MA (US); Alejandro J. Laguna Sanz, Cambridge, MA (US); Francis J. Doyle, III, Chestnut Hill, MA (US)

(73) Assignees: President and Fellows of Harvard College, Cambridge, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/069,865

(22) PCT Filed: Jan. 12, 2017

(86) PCT No.: PCT/US2017/013248
§ 371 (c)(1),
(2) Date: Jul. 12, 2018

(87) PCT Pub. No.: WO2017/123805
PCT Pub. Date: Jul. 20, 2017

(65) Prior Publication Data
US 2019/0035507 A1 Jan. 31, 2019

Related U.S. Application Data

(60) Provisional application No. 62/277,788, filed on Jan. 12, 2016.

(51) Int. Cl.
*G16H 50/50* (2018.01)
*A61M 5/172* (2006.01)
(Continued)

(52) U.S. Cl.
CPC ............ *G16H 50/50* (2018.01); *A61M 5/142* (2013.01); *A61M 5/172* (2013.01); *G06N 5/02* (2013.01);
(Continued)

(58) Field of Classification Search
CPC ....... G16H 50/50; G16H 50/30; A61M 5/172; A61M 2205/50; A61M 2230/201; A61M 2205/52; A61M 5/142; G06N 5/02
See application file for complete search history.

(56) References Cited

U.S. PATENT DOCUMENTS

2004/0158232 A1   8/2004   Schetky et al.
2007/0244575 A1   10/2007  Wojsznis et al.
(Continued)

FOREIGN PATENT DOCUMENTS

AU   2017206786 A1   8/2018
CA   3011231 A1     7/2017
(Continued)

OTHER PUBLICATIONS

Grosman et al "Zone Model Predictive Control: A Strategy to Minimize Hyper- and Hypoglycemic Events", Jul. 2010, pp. 961-975, downloaded from the internet https://journals.sagepub.com/doi/pdf/10.1177/193229681000400428 (Year: 2010).*
(Continued)

*Primary Examiner* — Rocio Del Mar Perez-Velez
*Assistant Examiner* — Olvin Lopez Alvarez
(74) *Attorney, Agent, or Firm* — Nixon Peabody LLP

(57) ABSTRACT

Presented herein are methods, and devices of adaptively tuning a zone based Model Predictive Control (MPC) con-
(Continued)

troller, using at least one processor, which include determining, residuals based on prediction models storing, in a memory, the determined residuals, calculating a trust index by quantifying uncertainty of the prediction models using the stored residuals and tuning the MPC controller, in real time based on the calculated value of the trust index.

11 Claims, 12 Drawing Sheets

(51) Int. Cl.
    *G06N 5/02*         (2006.01)
    *G16H 50/30*      (2018.01)
    *A61M 5/142*     (2006.01)

(52) U.S. Cl.
    CPC ......... *G16H 50/30* (2018.01); *A61M 2205/50* (2013.01); *A61M 2205/52* (2013.01); *A61M 2230/201* (2013.01)

(56) References Cited

U.S. PATENT DOCUMENTS

| | | | |
|---|---|---|---|
| 2007/0276512 A1* | 11/2007 | Fan | G05B 11/32 700/37 |
| 2008/0208113 A1* | 8/2008 | Damiano | A61M 5/1723 604/67 |
| 2010/0280441 A1 | 11/2010 | Wilinska et al. | |
| 2010/0298685 A1* | 11/2010 | Hayter | A61B 5/14532 600/365 |
| 2011/0106011 A1 | 5/2011 | Cinar et al. | |
| 2011/0208156 A1* | 8/2011 | Doyle, III | A61B 5/14532 604/504 |
| 2013/0018232 A1* | 1/2013 | D'Souza | A61B 6/12 600/300 |
| 2014/0081236 A1 | 3/2014 | Wilinska et al. | |
| 2014/0121488 A1 | 5/2014 | Budiman | |
| 2014/0180240 A1* | 6/2014 | Finan | A61M 5/1723 604/504 |
| 2014/0200559 A1* | 7/2014 | Doyle, III | A61M 5/1723 604/891.1 |
| 2014/0276554 A1* | 9/2014 | Finan | A61M 5/1723 604/504 |
| 2014/0276555 A1 | 9/2014 | Morales | |
| 2015/0100038 A1 | 4/2015 | McCann et al. | |
| 2015/0309486 A1* | 10/2015 | Webersinke | G05B 13/048 700/29 |
| 2016/0038673 A1* | 2/2016 | Morales | G06F 19/3468 700/282 |
| 2016/0048119 A1* | 2/2016 | Wojsznis | G05B 19/0423 700/11 |
| 2016/0170384 A1* | 6/2016 | Charest-Finn | G05B 13/026 700/44 |
| 2016/0281489 A1* | 9/2016 | Dykstra | E21B 44/02 |
| 2017/0017212 A1* | 1/2017 | Collins | G06N 3/084 |
| 2017/0192400 A1* | 7/2017 | Hofschulz | G05B 15/02 |
| 2018/0369479 A1* | 12/2018 | Hayter | A61M 5/1723 |

FOREIGN PATENT DOCUMENTS

| | | |
|---|---|---|
| CN | 108883227 A | 11/2018 |
| EP | 3402552 A1 | 11/2018 |
| JP | 2019506265 A | 3/2019 |
| RU | 51501 U1 | 2/2006 |
| RU | 59415 U1 | 12/2006 |
| WO | 2011146726 A1 | 11/2011 |
| WO | 2017123805 A1 | 7/2017 |

OTHER PUBLICATIONS

Gonzalez et al, "A stable MPC with zone control", 2009, pp. 110-122. downloaded from the internet https://reader.elsevier.com/reader/sd/pii/S0959152408000097?token=44E0E24B897AC2DAE 14D6030E5151F6877D1FF8BCE5656EFD1270A348260D425C65 C74FFA71B82B9AAE88AE7B18E34C8 (Year: 2009).*

Lee et al "A Closed-loop Artificial Pancreas based on MPC: human-friendly identification and automatic meal disturbance rejection", 2008, pp. 4252-4257. downloaded from the internet https://www.sciencedirect.com/science/article/pii/S1474667016396136 (Year: 2008).*

Charest et al ("MPC enhancement for trackingof complex profiles— The basictechnique", 2014 pp. 136-147, downloaded from internet https://www.sciencedirect.com/science/article/pii/S0967066114002317 (Year: 2014).*

Heusden et al "Control-Relevant Models for Glucose Control Using a Priori Patient Characteristics", 2012, pp. 1839-1849. Downloaded from IEEE databases (Year: 2012).*

Wang et al, "Automatic Bolus and Adaptive Basal Algorithm for the Artificial Pancreatic b-Cell", 2010, pp. 879-887, downloaded from the internet https://www.ncbi.nlm.nih.gov/pubmed/20879966 (Year: 2010).*

Seborg et al, "Chapter 20 Model Predictive Control", 2011, pp. 414-438 downloaded from the internet file:///C:/Users/olopez/Documents/e-Red%20Folder/16069865/seborg%20CH%2020%20Model%20Predictive%20Control.pdf (Year: 2011).*

Enso, "Model Predictive Control and State Estimation", Jan. 2013, pp. 112 downloaded from the internet http://cc.oulu.fi/~iko/SSKM/SSKM2016-MPC-SE.pdf (Year: 2013).*

Domanski et al, "Assessment of predictive control performance using fractal measures", Mar. 24, 2017 pp. 773-790, downloaded from the internet https://link.springer.com/content/pdf/10.1007/s11071-017-3484-3.pdf (Year: 2017).*

Lee et al, "Enhanced Model Predictive Control (eMPC) Strategy for Automated Glucose Control" Nov. 23, 2016, pp. 1-28, downloaded from the internet https://www.ncbi.nlm.nih.gov/pmc/articles/PMC5144164/pdf/nihms832141.pdf (Year: 2016).*

Cameron et al, "A Closed-Loop Artificial Pancreas Based on Risk Management" Mar. 2011, pp. 368-379, downloaded from the internet https://www.ncbi.nlm.nih.gov/pmc/articles/PMC3125931/pdf/dst-05-0368.pdf (Year: 2011).*

Messori et al, "A Constrained Model Predictive Controller for an Articial Pancreas", Aug. 2014, pp. 10144-10149, downloaded from the internet https://pdf.sciencedirectassets.com/314898/ . . . (Year: 2014).*

Tiagounov, "High-performance model predictive control for process industry", Jan. 1, 2004, pp. 180, downloaded from the internet https://pure.tue.nl/ws/files/3656513/200411301.pdf (Year: 2004).*

Gonzales et al, "Model Predictive Control Tuning Based on Extended Kalman Filter", Oct. 2017, pp. 6. downloaded from the internet https://ieeexplore.ieee.org/document/8247480 (Year: 2017).*

Soru et al, "MPC based Artificial Pancreas: Strategies for individualization and meal compensation", 2012, pp. 118-128. downloaded from the internet https://www.sciencedirect.com/science/article/pii/S1367578812000107 (Year: 2012).*

Sanz et al, "An Enhanced Model Predictive Control for the Artificial Pancreas Using a Confidence Index Based on Residual Analysis of Past Predictions", Dec. 1, 2016, pp. 8. downloaded from the internet https://www.ncbi.nlm.nih.gov/pmc/articles/PMC5505428/ (Year: 2016).*

Banerjee, A. "Model Based Safety Analysis and Verification of Cyber-Physical Systems", Dissertation, Arizona State University [online]. Published Nov. 2012 [retrieved Mar. 9, 2017]. Retrieved from the Internet:<URL: https://impact.asu.edu/-mcn/thesis/Banerjee_asu_0010E_12441.pdf>.

Hu et al., "An improved PID algorithm based on insulin-on-board estimate for blood glucose control with Type 1 diabetes." Computational and Mathematical Methods in Medicine 2015(281589):1-9 (2015).

International Search Report and Written Opinion for PCT/US2017/13248 dated Apr. 12, 2017, 8 pages.

International Preliminary Report on Patentability for PCT/US2017/13248 dated Jul. 17, 2018, 7 pages.

(56) References Cited

OTHER PUBLICATIONS

Extended Search Report for EP 17738968.1 dated Jun. 3, 2019, 11 pages.

* cited by examiner

FIG. 2

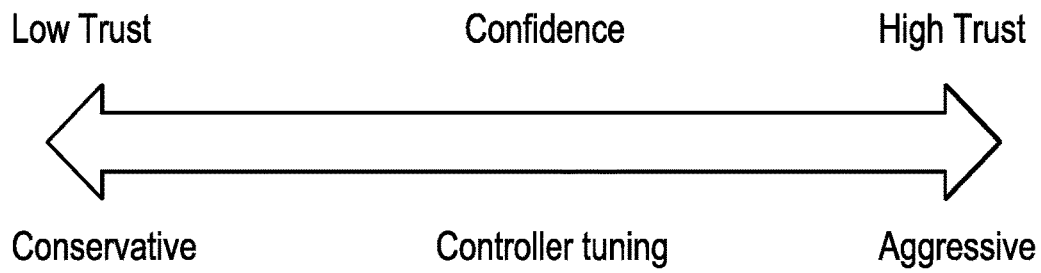

FIG. 3

Controller behavior for every glucose scenario and each trust index value

|  | High Trust Index | Low Trust Index |
|---|---|---|
| Hyperglycemia | Controller delivers insulin freely and aggressively | Controller refrains on acting aggressively, but still delivers insulin |
| Hypoglycemia | Controller reduces insulin delivery. Controller may deliver basal insulin if excursions are small and predicted glucose is rising | Controller shuts off the pump. May not deliver insulin even if model predictions indicate rising glucose levels |

FIG. 7

Performance metrics of the controller for aggressive, conservative and dynamic tuning. p-values shown for comparison against the adaptive tuning

| Tuning | Aggressive | Conservative | Adaptive |
|---|---|---|---|
| Average glucose [mg/dL (p-value)] | 142.9 (<0.005) | 153.7 (<0.005) | 149.3 |
| Time in range 70-180 [% (p-value)] | 77.3 (<0.005) | 71.9 (<0.005) | 74.7 |
| Time in hypo < 70 [% (p-value)] | 0.98 (<0.005) | 0.02 (0.38) | 0.06 |
| Time in hyper > 300 [% (p-value)] | 0.69 (<0.005) | 1.48 (0.34) | 1.4 |

FIG. 13

| Tuning | Adaptive | Default | Aggressive | Conservative |
|---|---|---|---|---|
| Bolus strategy | | | | |
| Average glucose [mg/dL (p value)] | 134 ± 6 | 134 ± 6 (.2) | 131 ± 6 (<.005) | 137 ± 7 (<.005) |
| Total insulin [IU (p value)] | 24.9 ± 5.6 | 24.8 ± 5.5 (.33) | 25.5 ± 5.8 (.0057) | 24.4 ± 5.5 (.03) |
| Time in target range 70-180 [% (p value)] | 91 ± 5.6 | 90.7 ± 5.9 (.16) | 92.3 ± 6.1 (<.005) | 89.8 ± 5.8 (<.005) |
| Time in hypoglycemia <70 [% (p value)] | 0 ± 0* | 0.01 ± 0.16 (<.005) | 0.1 ± 0.57 (<.005) | 0 ± 0 (1) |
| Time in hyperglycemia >300 [% (p value)] | 0.01 ± 0.13 | 0.01 ± 0.22 (.25) | 0.01 ± 0.21 (.22) | 0 ± 0 (.08) |
| GRID strategy | | | | |
| Average glucose [mg/dL (p value)] | 149 ± 10* | 147 ± 8 (<.005) | 143 ± 7 (<.005) | 154 ± 13 (<.005) |
| Total insulin [IU (p value)] | 23.4 ± 5.2* | 23.8 ± 5.1 (.03) | 24.5 ± 5.8 (<.005) | 22.8 ± 5.1 (0.1) |
| Time in target range 70-180 [% (p value)] | 74.6 ± 6.9 | 75 ± 7.1 (.12) | 77 ± 7.2 (<.005) | 71.2 ± 9.4 (<.005) |
| Time in hypoglycemia <70 [% (p value)] | 0.16 ± 0.84* | 0.67 ± 1.82 (<.005) | 1.04 ± 2.43 (<.005) | 0.15 ± 1 (.44) |
| Time in hyperglycemia >300 [% (p value)] | 1.07 ± 2.84 | 1.02 ± 2.31 (.34) | 0.7 ± 1.62 (<.005) | 1.37 ± 3.5 (.02) |

PREDICTIVE CONTROL MODEL FOR THE ARTIFICIAL PANCREAS USING PAST PREDICTIONS

CROSS REFERENCE TO RELATED APPLICATIONS

This application is a 371 National Phase Entry of International Patent Application No. PCT/US2017/013248 filed on Jan. 12, 2017, which designates the U.S., and which claims benefit under 35 U.S.C. § 119(e) of U.S. Provisional Application No. 62/277,788 filed Jan. 12, 2016, the contents of which are incorporated herein by reference in their entirety.

GOVERNMENT SUPPORT

This invention was made with Government support under DK104057 and DK094331 awarded by the National Institutes of Health. The Government has certain rights in this invention.

BACKGROUND

Technical Field

The present disclosure relates generally to model predictions of glucose concentration for artificial pancreas. More particularly, aspects of this disclosure relate to methods, and devices directed towards an adaptive model predictive controller to improve model prediction accuracy.

Description of Related Art

The destruction of the insulin secretion pancreatic beta-cells in people with type 1 diabetes mellitus causes glucose concentration to increase to unhealthy threatening levels in the bloodstream. Prolonged high blood glucose concentration is harmful to the patient, making an exogenous insulin delivery a necessity. However, excessive insulin delivery is also dangerous, since too low glucose concentration (hypoglycemia) can quickly lead to coma or even death. The most common treatment historically has been Multiple Daily Injections (MDI) of insulin to correct the ever-increasing glucose concentration. Even though MDI is still the most applied treatment, the introduction of Continuous Subcutaneous Insulin Infusion (CSII) pumps and Continuous Glucose Monitors (CGM) in the last decades has boosted the application of a variety of new, more efficient insulin-based treatments.

The artificial pancreas is a device that aims to automate insulin delivery (close the loop) by continuously adjusting insulin delivery based on glucose fluctuations. Massive advances have been done in recent years with several research teams completing closed-loop experiments in controlled environments, and more recently in an ambulatory setting and even free living/at home.

The core of any artificial pancreas is a control algorithm that calculates the appropriate insulin dosing to maintain glucose concentration at a safe healthy level at all times. The most common controllers used in the artificial pancreas are algorithms based on: Model predictive control (MPC), Proportional-Integral-Derivative (PID) approach and Fuzzy-Logic design.

MPC controllers use prediction models to estimate the trajectories of output variables. However, glucose predictions by mathematical models are still very inaccurate, and model individualization is unsatisfactory for data-based models or physiology-based models, resulting in great uncertainty in the model predictions for individual patients. Several recent studies about the quantification of the uncertainty have been published by bounding the uncertainty using interval identification, showing very promising results.

MPC performance depends on the accuracy of the prediction models implemented for the controller. Prediction errors must be measured and accounted for in the glucose regulation process. Thus, there is a need for an MPC algorithm that is personalized to the patient's clinical information and an MPC with a reference defined as a glucose zone, designed to deliver the optimal insulin dose that brings glucose predictions to a healthy range within a limited time frame.

SUMMARY

According to an aspect of an exemplary embodiment, a method of adaptively tuning a zone based Model Predictive Control (MPC) controller, using at least one processor, includes determining, using at least one of said at least one processor, residuals based on prediction models, storing, in a memory, the determined residuals, calculating a trust index, using at least one of said at least one processor, by quantifying uncertainty of the prediction models using the stored residuals and tuning the MPC controller, in real time, using at least one of said at least one processor, based on the calculated value of the trust index.

According to another exemplary embodiment the determining further includes determining the residual at time t and for a prediction k steps ahead using the formula:

$$res_k^t = y_{k|t-k} - CGM_t \ \forall k \in \mathbb{Z}$$

where $y_{k|t-k}$ represents predicted glucose by the model at time t that was predicted k samples in the past, $N_p$ represents prediction horizon and $CGM_t$ represents current glucose values.

According to another exemplary embodiment the storing further comprises storing each of the $N_p$ residuals ($res_k^t$) in a pool of most recent $N_f$ residuals, resulting in a matrix $N_p \times N_f$.

According to another exemplary embodiment, the method further includes penalizing, using at least one of said at least one processor, the determined residuals using a forgetting function, where the forgetting function is determined using the formula:

$$\widetilde{res}_{k,i}^t = res_k^{t-i} \cdot \frac{\log(N_f - i + 1)}{\log N_f} \ \forall i \in \mathbb{Z}_1^{N_f}, \forall k \in \mathbb{Z}_1^{N_p}$$

where t represents current time, $res_k^{t-i}$ represent progressively more distant residuals, and $\widetilde{res}_{k,i}^t$ represents the penalized residual.

According to another exemplary embodiment, for each timestamp t each residual is penalized differently.

According to another exemplary embodiment, the tuning further comprises tuning the MPC conservatively when the determined residuals have a high value.

According to another exemplary embodiment, the tuning further comprises tuning the MPC conservatively when the penalized residuals have a high value.

According to another exemplary embodiment, the tuning further comprises tuning the MPC aggressively when the determined residuals have a low value.

According to another exemplary embodiment, the tuning further comprises tuning the MPC aggressively when the penalized residuals have a low value.

According to another exemplary embodiment, the method further includes calculating, using at least one of said at least one processor, an estimate of a confidence interval of a current prediction error based on the penalized residuals using the formula:

$$B_x = \max(\text{percentile}_x(\widetilde{res}_k^t), 0) \; \forall k \in \mathbb{Z}_1^{N_p}$$

where $B_k$ is an empirically defined boundary of the confidence interval of a prediction error k steps ahead, and $\text{percentile}_x(\widetilde{res}_k^t)$ represents x-th percentile function of the penalized residual at time t and for a prediction k steps ahead.

According to another exemplary embodiment, the calculating the estimate of the confidence interval comprises calculating an empirically defined upper boundary $\hat{B}_k$ and an empirically defined lower boundary $\check{B}_k$ using the formula:

$$\hat{B}_k = \max(\text{percentile}_{95}(\widetilde{res}_k^t), 0) \; \forall k \in \mathbb{Z}_1^{N_p}$$

$$\check{B}_k = \min(\text{percentile}_s(\widetilde{res}_k^t), 0) \; \forall k \in \mathbb{Z}^{N_p}$$

According to another exemplary embodiment, the calculating the trust index comprises calculating the trust index based on the calculated empirically defined upper boundary $\hat{B}_k$ and the calculated empirically defined lower boundary $\check{B}_k$ using the formula:

$$T_t := \hat{B}_k - \check{B}_k + d_H\left(CGM_t, [\check{B} + y_t, \hat{B} + y_t]\right)$$

$$d_H(x, [a, b]) := \begin{cases} 0 & \text{if } x \in [a, b] \\ x - b & \text{if } x > b \\ a - x & \text{if } x < a \end{cases}$$

where $d_H(x, [a, b])$ represents Hausdorff distance from a point x to an interval [a, b], and $y_t$ represents model's prediction of current CGM sample.

According to another aspect of an exemplary embodiment, a method of insulin delivery using an artificial pancreas, the artificial pancreas including at least one processor, includes determining, using at least one of said at least one processor, residuals based on prediction models, storing, in a memory, the determined residuals, calculating a trust index, using at least one of said at least one processor, by quantifying uncertainty of the prediction models using the stored residuals, tuning a model prediction control (MPC) controller, in real time, using at least one of said at least one processor, based on the calculated value of the trust index, and controlling, using at least one of said at least one processor, the delivery of insulin based on the tuned MPC controller.

According to another aspect of an exemplary embodiment, an artificial pancreas apparatus for insulin delivery includes at least one non-transitory memory operable to store program code, a model prediction control (MPC) controller including at least one processor operable to read said program code and operate as instructed by said program code, said program code causing the at least one processor to determine residuals based on prediction models, store, in the at least one non-transitory memory, the determined residuals, calculate a trust index by quantifying uncertainty of the prediction models using the stored residuals, tune the MPC controller in real time based on the calculated value of the trust index, and deliver the insulin based on the tuned MPC controller.

BRIEF DESCRIPTION OF THE DRAWINGS

FIG. 2 depicts a relationship between confidence on the current measurement and the aggressiveness of the current tuning, according to the adaptive MPC controller.

FIG. 3 depicts a table describing controller behavior based on the glucose scenario and trust index value, according to an exemplary embodiment.

FIG. 7 depicts a table providing a performance comparison metric of an MPC controller tuned aggressively, conservatively and adaptively, according to an exemplary embodiment.

FIG. 13 depicts the Mean and standard deviation of the control performance metrics of the zMPC controller for the Default, Aggressive, Conservative, and Adaptive tuning, according to an exemplary embodiment.

Figure 1:
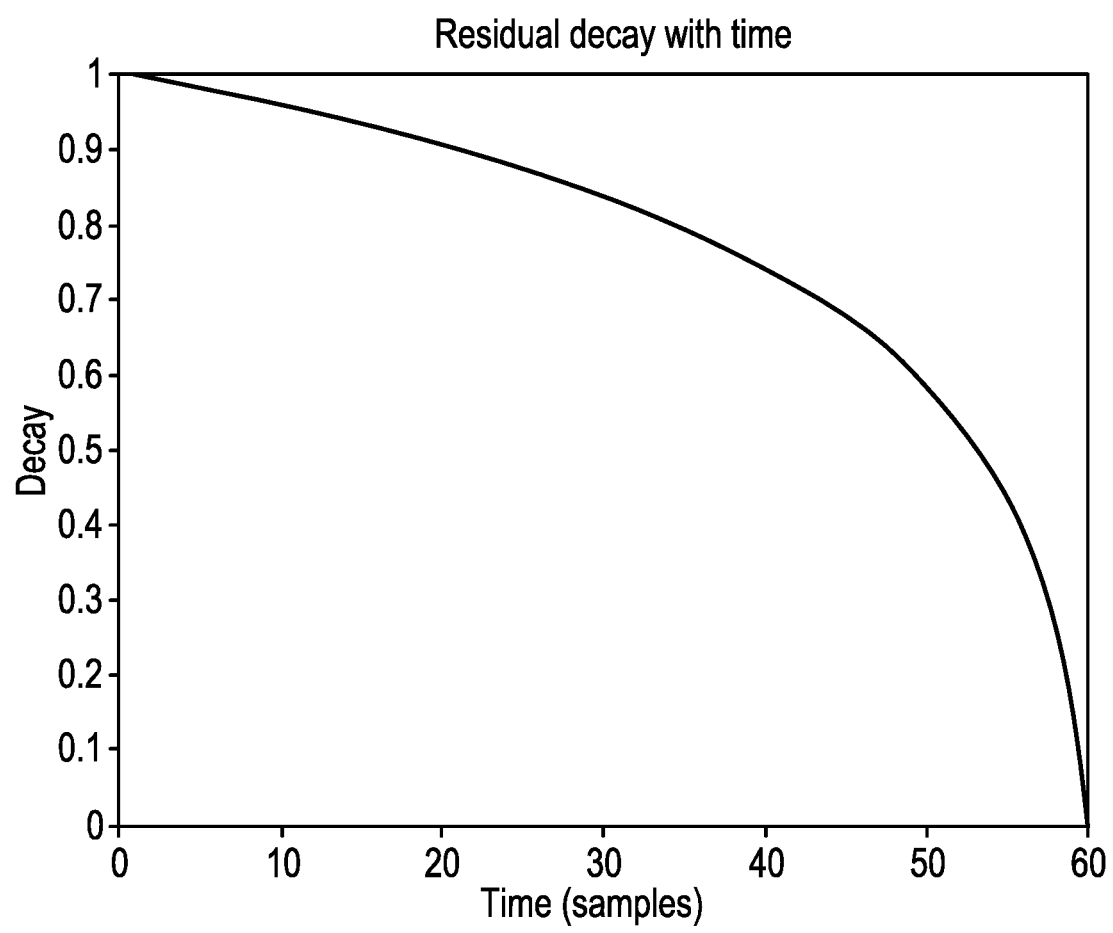
FIG. 1 depicts a logarithmic forgetting function applied to the residuals, according to an exemplary embodiment.

The present disclosure is susceptible to various modifications and alternative forms, and some representative embodiments have been shown by way of example in the drawings and will be described in detail herein. It should be understood, however, that the inventive aspects are not limited to the particular forms illustrated in the drawings. Rather, the disclosure is to cover all modifications, equivalents, and alternatives falling within the spirit and scope of the disclosure as defined by the appended claims.

DETAILED DESCRIPTION OF THE DRAWINGS

Embodiments will be described below in more detail with reference to the accompanying drawings. The following detailed descriptions are provided to assist the reader in gaining a comprehensive understanding of the methods, apparatuses, and/or systems described herein and equivalent modifications thereof. Accordingly, various changes, modifications, and equivalents of the methods, apparatuses, and/or systems described herein will be apparent to those of ordinary skill in the art. Moreover, descriptions of well-known functions and constructions may be omitted for increased clarity and conciseness.

The terms used in the description are intended to describe embodiments only, and shall by no means be restrictive. Unless clearly used otherwise, expressions in a singular from include a meaning of a plural form. In the present description, an expression such as "comprising" or "including" is intended to designate a characteristic, a number, a step, an operation, an element, a part or combinations thereof, and shall not be construed to preclude any presence or possibility of one or more other characteristics, numbers, steps, operations, elements, parts or combinations thereof.

It will be understood to those skilled in the art that the disclosure described herein may apply to any type of special-purpose or general-purpose computer, including a standalone computer or portion thereof.

The present disclosure describes quantifying the model prediction accuracy by a rigorous analysis of the prediction residuals, and calculating a "Trust Index," to be used as a tuning tool in a closed-loop algorithm. The integration of the information from the prediction residuals into the control algorithm is used to achieve a new generation of adaptive control algorithms. These algorithms act aggressively to eliminate both hyper-glycemia and hypo-glycemia in case of good confidence in the glucose profile, determined by a continuous glucose monitor (CGM) according to an exemplary embodiment, and act conservative in case of poor CGM quality, in-turn providing a safer and more effective glucose control.

The above described results may be achieved by calculating optimal insulin dosage by solving an optimization problem in which a scalar index is minimized by penalizing relative input deviations and glucose predictions out of the reference zone. The controller's tuning parameters are the penalizations of the input variable (insulin). Positive and negative relative inputs may be penalized differently, as will be described in greater detail below.

The in silico simulations and results analyzed in the various figures below were achieved using Matlab R2013b (Mathworks, Natick, Mass.) as the platform. However, other such programs might be used for the same simulations and analysis. The p-values for statistical comparison where calculated using non-parametric random permutations methods. The datasets were generated using the Universities of Virginia/Padova metabolic simulator, which has been accepted by the FDA in lieu of animal trials. The simulator implements ten parameter combinations that represent the inter-patient variability equivalent to the general diabetic population. A key part of the simulator is a model of the CGM noise based on different probabilistic distributions. The CGM error is different for each execution of the software, introducing an even larger variability in every simulation, even for simulations of the same in silico patient. The variability introduced by the random number generator for each simulation impedes a clear comparison of the ten in silico patients under different treatments. To minimize this effect, every in silico subject is simulated ten times under every scenario to sum a total of 100 datasets. By doing this, the noise introduced by the CGM error model is averaged over the different simulations of each in silico subject, while still maintaining the variability that the CGM model introduces on the experiments. The above described scenarios are used as exemplary embodiment to achieve simulations and compare results between statically and adaptively tuned MPC controlled. It should be noted that the disclosure is not limited to the above exemplary embodiment and different datasets, simulators and methods may be used to achieve the simulations and results.

The simulations, under this exemplary embodiment depicted in the drawings, consist in twenty four hours of CGM data with three unannounced meals of increasing carbohydrates load (50 g, 75 g and 100 g). Every simulation was preceded by two hours of open-loop monitoring as a warm up period. During that time the in silico subject received the appropriate basal insulin. In order to minimize the postprandial glucose excursion a meal detection algorithm was used (Glucose Rate Increase Detector, GRID). This algorithm triggered an alarm when certain conditions of glucose concentration and glucose trend were met, and an insulin compensation dose was administered, equivalent to a prandial bolus strategy. The compensation bolus was the equivalent to a 75 g carbohydrate (CHO) meal correction, based on the patient's insulin-to-carbohydrate ratio. GRID also incorporates routines for patient safety including an algorithm that avoids delivering extra insulin according to recent insulin delivery history, and a security interlock in case of missing CGM samples.

The chosen controller, Zone MPC controller (zMPC), was developed originally by Grosman et al. using a constant glucose reference band, and implementing very simple models for the insulin and meal inputs to the system. This control scheme was later expanded by improving the prediction model, using a control oriented prediction strategy proposed by van Heusden et al. Further functionalities were added to the controller and to the prediction model by Gondhalekar et al, implementing different penalization weights for insulin delivery larger or smaller than the patient's basal rate. The cost function for the MPC problem is explained below. The formulae provided below are based on the conventional controllers provided in the above references:

$$J(\cdot) := \sum_{k=1}^{N_p} z_k^2 + \sum_{k=0}^{N_u-1} \left( \hat{R}\hat{u}_k^2 + \check{R}\check{u}_k^2 \right) \quad\quad 1$$

$$\hat{u}_k := \max(u_k - u_{BASAL}, 0) \; \forall \, k \in \mathbb{Z}_0^{N_u-1} \quad\quad 2$$

$$\check{u}_k := \min(u_k - u_{BASAL}, 0) \; \forall \, k \in \mathbb{Z}_0^{N_u-1} \quad\quad 3$$

where $N_p$ prediction horizon, and $N_u$ is the control horizon and $z_k$ is the output error, understood as the distance of the glucose prediction to the glucose safe zone. $u_k$ is the insulin input, and $u_{BASAL}$ is the patient's basal insulin.

The current disclosure describes using $\hat{R}$ and $\check{R}$ parameters to adaptively tune the controller. Both parameters modulate the insulin delivery, but $\hat{R}$ penalizes insulin actions greater than the basal rate of the patient, while $\check{R}$ acts on the insulin action when it is being suppressed below basal rate. Increasing the value of $\hat{R}$ penalizes higher insulin values and tends to make the controller more conservative, delivering less insulin. Increasing the value of $\check{R}$ impedes insulin attenuation/suspension, tending to give more insulin, making the controller more aggressive.

An aggressive controller is prone to deliver more insulin. It would act fast to counter hyperglycemic excursions, and it would be slow to suspend insulin infusion in presence of hypoglycemia.

On the other hand, a conservative controller delivers less insulin overall. It shuts down pump infusion fast to minimize hypoglycemia, but it reacts slow to hyperglycemic excursions.

According to an exemplary embodiment, two different sets of parameters are selected: 1) very aggressive design $\hat{R}=500$, $\check{R}=300$; 2) very conservative design $\hat{R}=50000$, $\check{R}=10$. These will be used to compare the simulation results between statically tuned and adaptively tuned MPC controllers.

It should be noted that the ratio between $\hat{R}$ and $\check{R}$ provides a measurement of the asymmetry of the controller, but this ratio is not enough to characterize the aggressiveness of the controller. The magnitude of $\hat{R}$ and $\check{R}$ separately penalizes the input costs (as shown in equation 1) relatively to the weight of the output error, which is fixed.

Referring now to the drawings, wherein like reference numerals refer to like features throughout the several views, there is shown in FIG. 1, a logarithmic forgetting function applied to the residuals, according to an exemplary embodiment.

The method and device described in the current disclosure to quantify the trust of the model prediction makes use of the available information provided by the residuals of the predictions of that same model. Each of the $N_p$ residuals ($res_k^t$) is stored in a pool of the most recent $N_f$ residuals, resulting in a matrix $N_p \times N_f$. The residual at time t and for a k steps ahead prediction is defined as:

$$res_k^t = y_{k|t-k} - CGM_t \quad \forall k \in \mathbb{Z}_1^{N_p} \quad \quad 4$$

where $y_{k|t-k}$ is the predicted glucose by the model at time t that was predicted k samples in the past. $CGM_t$ is the current glucose values. The residuals are penalized using the forgetting function:

$$\check{res}_{k,i}^t = res_k^{t-i} \cdot \frac{\log(N_f - i + 1)}{\log N_f} \quad \forall i \in \mathbb{Z}_1^{N_f}, \forall k \in \mathbb{Z}_1^{N_p} \quad \quad 5$$

where t stands for the current time, $res_k^{t-i}$ are the progressively more distant residuals, and $\check{res}_{k,i}^t$ is its analog penalized residual. Note that for each timestamp t each of the residuals is penalized differently. More recent residuals are considered equally meaningful in the pool of residuals, and the relevance of older residuals decays fast when approaching the limit $N_f=60$ samples. The normalized decay function is depicted in FIG. 1. It should be noted that the depicted normalized forgetting function is merely an exemplary embodiment and both the limit and the forgetting function can be altered if required for testing of other algorithms, per the choice of the designer.

As can be seen in FIG. 1, a residual decay is depicted by potting the decay over time, according to an exemplary embodiment.

If the calculated residuals are very large, the predictions are considered to be poor and the tuning of the controller is considered at its best when it is relaxed, i.e. conservative. On the other hand, if the residuals are low, a more aggressive approach towards tuning the controller is preferred.

Every row ($\check{res}_k^t$) of the penalized residuals comprises an empirical sample of the probabilistic distribution of errors of the prediction model at current time t and predicted k samples before. A good estimation of the confidence interval of the current prediction error can be calculated from the fifth and ninety-fifth percentiles, according to an exemplary embodiment, of this sample. The below formulae provide the definition of intervals from residual distribution:

$$\hat{B}_k = \max(\text{percentile}_{95}(\check{res}_k^t), 0) \quad \forall k \in \mathbb{Z}_1^{N_p} \quad \quad 6$$

$$\check{B}_k = \min(\text{percentile}_5(\check{res}_k^t), 0) \quad \forall k \in \mathbb{Z}_1^{N_p} \quad \quad 7$$

where $\hat{B}_k$ and $\check{B}_k$ are the empirically defined upper and lower boundaries of the confidence interval of the k steps ahead prediction error, and $\text{percentile}_x(\cdot)$ is the x-th percentile function. Both boundaries are defined strictly positive or negative in order to smooth the initialization of the algorithm. Note that both boundaries are dependent on the residual pool at the current time t, so they must be considered as time-varying values. For simplicity, the sub-index k is dropped from now on, and only the first row of the residuals pool is used for the calculation of the trust index. Similarly, only the one step-ahead prediction is considered relevant hereinafter, however the disclosure is not limited thereto.

The trust index function is designed to obtain a scalar value that comprises both the uncertainty of the previous model predictions and the coherence of the new measurement with that uncertainty. The trust index may be calculated as follows:

$$T_t := \hat{B} - \check{B} + d_H(CGM_t, [\check{B} + y_t, \hat{B} + y_t]) \quad \quad 8$$

$$d_H(x, [a, b]) := \begin{cases} 0 & \text{if } x \in [a, b] \\ x - b & \text{if } x > b \\ a - x & \text{if } x < a \end{cases} \quad \quad 9$$

where $d_H(x, [a, b])$ stands for the Hausdorff distance from a point x to an interval [a, b], and $y_t$ stands for the model's prediction of the current CGM sample. The trust index is low whenever the confidence interval is small, and it grows whenever the boundaries grow, or if the current experimental measurement falls out of the bounds. The boundaries are not fixed either, and eventually, will grow whenever enough measurements fall out of the bounds, permanently increasing the trust index (until the forgetting algorithm catches up). A very high confidence is defined by design at $$T_t \leq 5 \left[\frac{mg}{dL}\right]$$

and the lowest possible confidence corresponds to a trust index value of $$T_t \geq 30 \left[\frac{mg}{dL}\right].$$

FIG. 2 depicts a relationship between confidence on the current measurement and the aggressiveness of the current tuning, according to the adaptive MPC controller.

The trust index in FIG. 2 is implemented into the closed-loop scheme presented by relating it to the aggressiveness tuning of the controller, as illustrated in FIG. 2.

As can be seen in FIG. 2, a high trust confidence rating corresponds to an aggressive tuning of the MPC controller and a low trust confidence rating corresponds to a conservative tuning of the MPC controller.

Every possible scenario of the correlation between the trust index and the controller aggressiveness is explained in the table depicted in FIG. 3.

FIG. 3 depicts a table describing controller behavior based on the glucose scenario and trust index value, according to an exemplary embodiment.

As can be seen in FIG. 3, under a high trust index the controller delivers insulin freely and aggressively to prevent hyperglycemia, and the controller reduces insulin delivery and may deliver basal insulin if excursions are small and predicted glucose is rising to prevent hypoglycemia. On the other hand, under a low trust index, the controller refrains on acting aggressively, but still delivers insulin to prevent hyperglycemia, and the controller shuts off the pump and may not deliver insulin even if model predictions indicate rising glucose levels to prevent hypoglycemia.

According to an exemplary embodiment, for a $T_t \leq 5$ mg/dL (high trust on the predictions) the aggressive tuning is selected, that is, $\hat{R}=800$, $\check{R}=500$. On the other hand, when the index surpasses the upper limit $T_t \geq 30$ mg/dL, the conservative tuning is used: $\hat{R}=50000$, $\check{R}=10$. Anywhere in between those thresholds both $\hat{R}$ and $\check{R}$ are linear functions of $T_t$ for every time stamp t, that is, the controller gains are updated in real time as $T_t$ is updated. This dependence of the tuning parameters on $T_t$, which ultimately makes them dependent on time, is what defines the aggressiveness tuning as adaptive. A graphical representation of the adaptation of both parameters, according to the exemplary embodiment, is discussed in more detail below with reference to FIG. 12.

Figure 4:
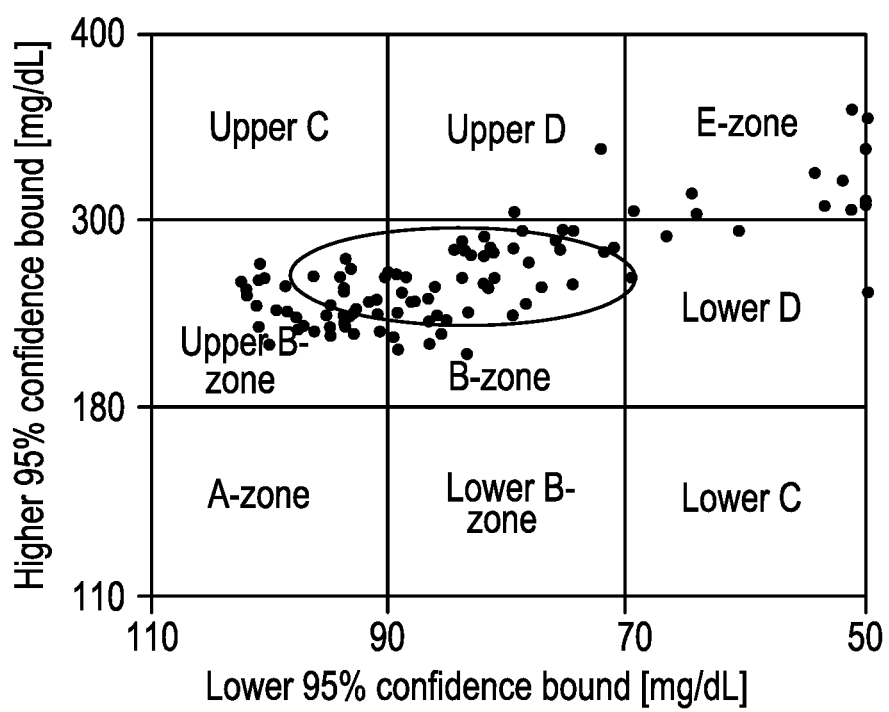
FIG. 4 depicts a control variability grid analysis for 10 in silico subjects from the UVA/Padova metabolic simulator using an aggressive tuning of the MPC controller, according to an exemplary embodiment.
Figure 5:
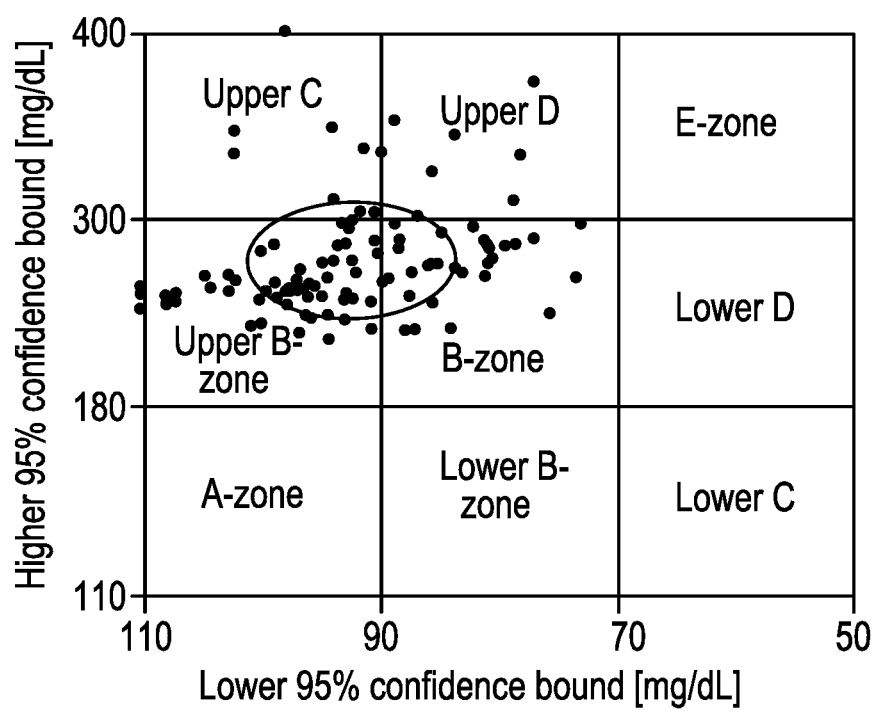
FIG. 5 depicts a control variability grid analysis for 10 in silico subjects from the UVA/Padova metabolic simulator using a conservative tuning of the MPC controller, according to an exemplary embodiment.
Figure 6:
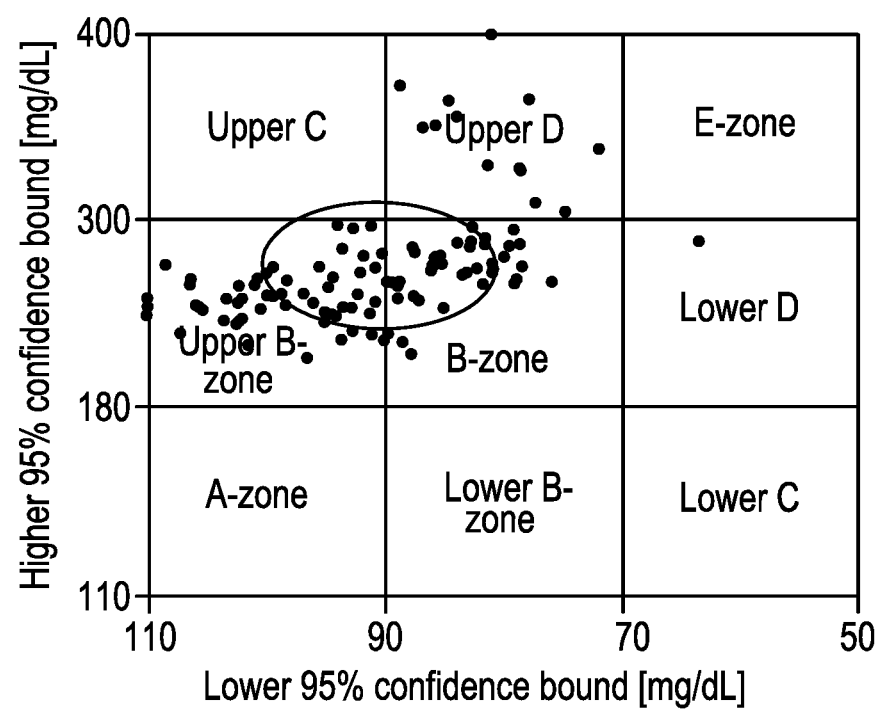
FIG. 6 depicts a control variability grid analysis for 10 in silico subjects from the UVA/Padova metabolic simulator using an adaptive tuning of the MPC controller, according to an exemplary embodiment.

While referencing FIGS. 4, 5 and 6 results of using a aggressively tuned, a conservatively tuned and an adaptively tuned MPC controller will be compared.

As discussed above, according to an exemplary embodiment, for a trust index value of $$T_t \leq 5\left[\frac{mg}{dL}\right]$$

the aggressive tuning for the asymmetrical MPC controller is selected, i.e. $\hat{R}=500$, $\check{R}=300$. On the other hand, when the index surpasses the upper limit $$T_t \geq 30\left[\frac{mg}{dL}\right],$$

the conservative tuning is used, i.e. $\hat{R}=50000$, $\check{R}=10$. Anywhere in between both controller parameters are tuned linearly with $T_t$ for every timestamp t.

The simulations performed using the UVA/Padova simulator aim at comparing the dynamic modulation of the tuning parameters of the MPC controller (adaptively tuned) to the two static MPC tuning states described above as "aggressive" and "conservative".

FIG. 4 depicts a control variability grid analysis for 10 in silico subjects from the UVA/Padova metabolic simulator using an aggressive tuning of the MPC controller, according to an exemplary embodiment.

The control variability grid analysis chart for the "aggressive" controller scheme is shown in FIG. 4, with hyper- and hypo-glycemia events (E-zone) reported for 12/100 simulations, while the mean and 1-sigma ellipse falls completely within the B-zone, considered safe.

FIG. 5 depicts a control variability grid analysis for 10 in silico subjects from the UVA/Padova metabolic simulator using a conservative tuning of the MPC controller, according to an exemplary embodiment.

In FIG. 5, the control variability grid analysis chart for the "conservative" controller is shown, displaying not a single simulation in the E-zone, but 8 simulations where located in zone C and 8 in zone D. The centroid is displaced to the left with respect to the case displayed in FIG. 4, as expected from a more conservative controller.

FIG. 6 depicts a control variability grid analysis for 10 in silico subjects from the UVA/Padova metabolic simulator using an adaptive tuning of the MPC controller, according to an exemplary embodiment.

In FIG. 6, the control variability grid analysis chart for the adaptive scheme is displayed. As with the conservative case, no simulations are placed in the E-zone, but 15/100 simulations fall in the D-zone. The centroid is displaced to the left slightly less than that in the case of FIG. 5.

Metrics are reported as mean plus-minus standard deviation of the in silico population. The performance metrics for the "default," "aggressive," and "conservative" tuning are statistically compared to the proposed adaptive algorithm. In the bolus strategy, the adaptive controller shows very similar performance (in mean glucose and time in range) to that of the "default" controller. However, the adaptive strategy is able to reduce significantly the time spent in hypoglycemia (0.01% vs 0.0%, p<0.005). Hypoglycemia is also rarely seen when using the conservative controller, but at the cost of a higher average glucose (137 mg/dL vs 134 mg/dL, p<0.005).

In the GRID scenario, the adaptive algorithm shows significantly lower average glucose than the conservative tuning (149 mg/dL vs 154 mg/dL, p<0.005). Furthermore, the proposed algorithm shows a significant reduction in hypoglycemia with respect to the aggressive case (0.16% vs 1.04%, p<0.005), with minimal increase in average glucose and good time in the safe glucose range. The time in hypoglycemia is not different for the conservative case and the proposed adaptive algorithm. Time in hypoglycemia for the proposed adaptive algorithm is significantly lower than for the default controller (0.16% vs 0.67%, p<0.005), but in this case at the cost of a higher average glucose. However, the time in range for the proposed algorithm is not significantly different than that of the default tuning. Performance metrics for the above described exemplary embodiment is further discussed later, in reference to FIG. 13.

For a complete comparison, the mean glucose, time in target range, time in hypoglycemia and time in hyperglycemia for the whole cohort of the in silico population is depicted in the table in FIG. 7. FIG. 7 depicts a table providing a performance comparison metric of an MPC controller tuned aggressively, conservatively and adaptively, according to an exemplary embodiment. The performance metrics for both the "aggressive" and "conservative" tuning are statistically compared to the adaptive algorithm.

As can be seen in FIG. 7, the adaptive algorithm shows significantly lower average glucose than the conservative tuning. The adaptive algorithm furthermore, shows a significant reduction in hypoglycemia with respect to the aggressive case, with minimal increase in average glucose and good time in the safe glucose range. The time in hypoglycemia is not different for the conservative case and the adaptive algorithm. The time in hyperglycemia is no better for the adaptive controller than it is for the conservative case, and the aggressive controller improves over the other two cases significantly.

The control variability grid analysis chart for the aggressive tuning in FIG. 4 shows a very different performance than those of the conservative and adaptive controllers (FIGS. 5 and 6), with multiple cases of mild and severe hypoglycemia. However, little information can be extracted by comparing the conservative and adaptive controllers. Both figures are very similar, with the centroid and the deviation ellipse being placed in a very similar position. However, when looking at FIG. 7, the adaptive tuning of the controller parameters shows better performance, clearly decreasing the average glucose from 153.7 mg/dL to 149.3 mg/dL, while increasing the time in range (70-180 mg/dL) from 71.9% to 74.7%. The numerical results also show that there is no significant difference between the time spent in hypoglycemia (BG<70 mg/dL) for the conservative tuning at 0.02% and the adaptive tuning at 0.06%. Control variability grid analysis charts are usually very informative for spotting severe hypoglycemia cases and large glucose excursions. This is especially true in the postprandial periods where glucose can reach very high levels. However, the information control variability grid analysis charts provide may be insufficient to assess the performance of a long term controller.

The results for the adaptive tuning are very promising as indicated in FIG. 7, improving the performance of the existing conservative controller without increasing the risk of hypoglycemia to the patient. The time in range is still not as good as it is for the aggressive controller, but the aggressive scenario supposed a much greater danger to the patient than the adaptive case in terms of hypoglycemic risk. The exemplary embodiment of the trust index implemented in this controller allows achievement of better control for the user by good use of already available information and without any additional risk to the patient's health.

Figure 8:
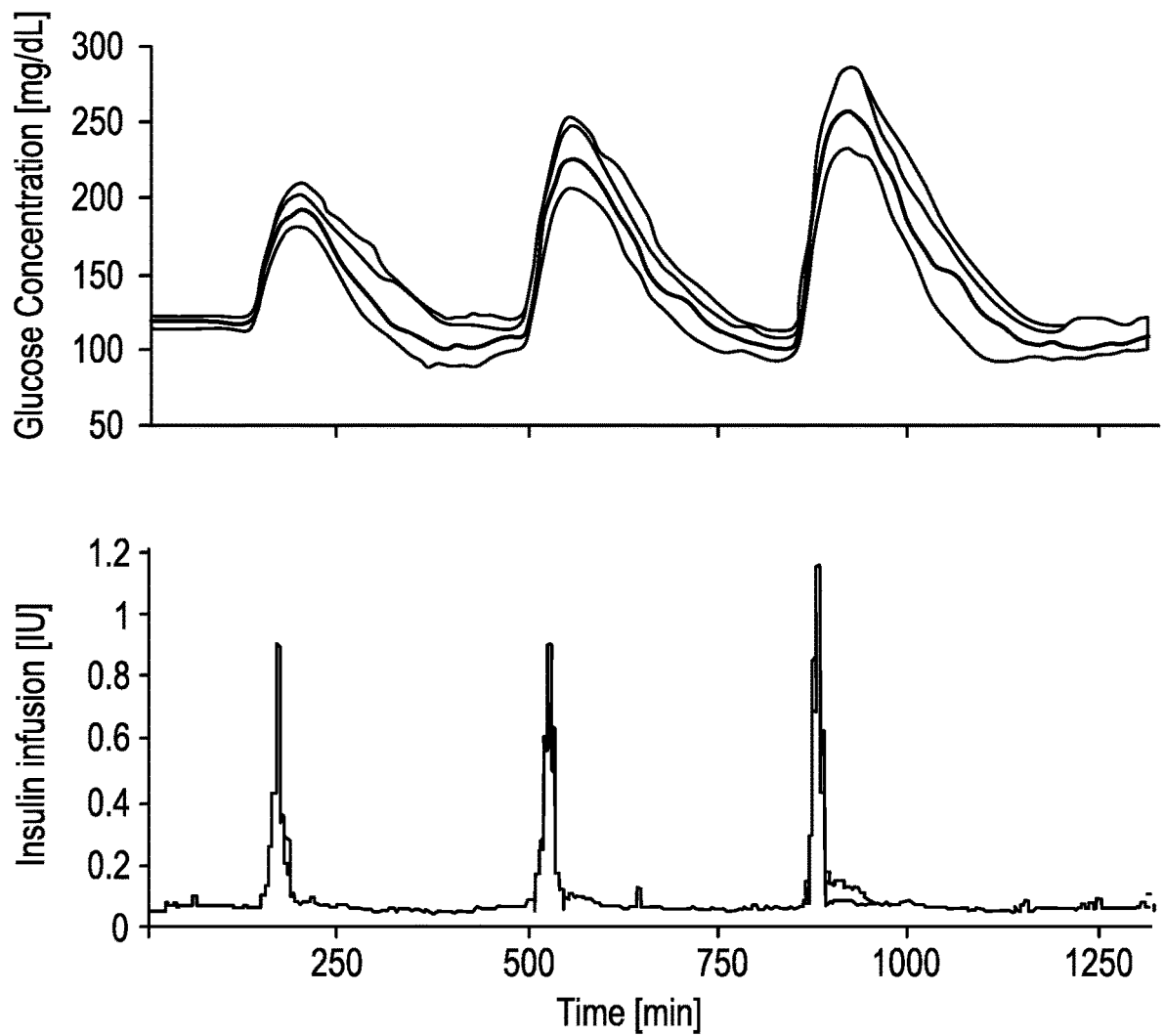
FIG. 8 depicts a chart providing a comparison in median glucose concentration and interquartile range (top) and mean insulin pump administration (bottom) between aggressive static tuning (plotted in blue—continuous line) and adaptive tuning (plotted in yellow—discontinuous line) of an MPC controller, the simulated protocol including three unannounced meals compensated using the glucose rate increase detector (GRID) meal detection algorithm, according to an exemplary embodiment.

FIG. 8 depicts a chart providing a comparison in median glucose concentration and interquartile range (top) and mean insulin pump administration (bottom) between aggressive static tuning (plotted in blue—continuous line) and adaptive tuning (plotted in yellow—discontinuous line) of an MPC controller, the simulated protocol including three unannounced meals compensated using the glucose rate increase detector (GRID) meal detection algorithm, according to an exemplary embodiment.

In FIG. 8 the glucose concentration and insulin infusion of the adaptive scenario and the aggressive controller are plotted overlapping the interquartile range. The insulin bolus delivered after the meals is evident for the three unannounced meals, showing very clear spikes shortly after the meal ingestion, as the algorithm takes some time to detect each meal.

Figure 9:
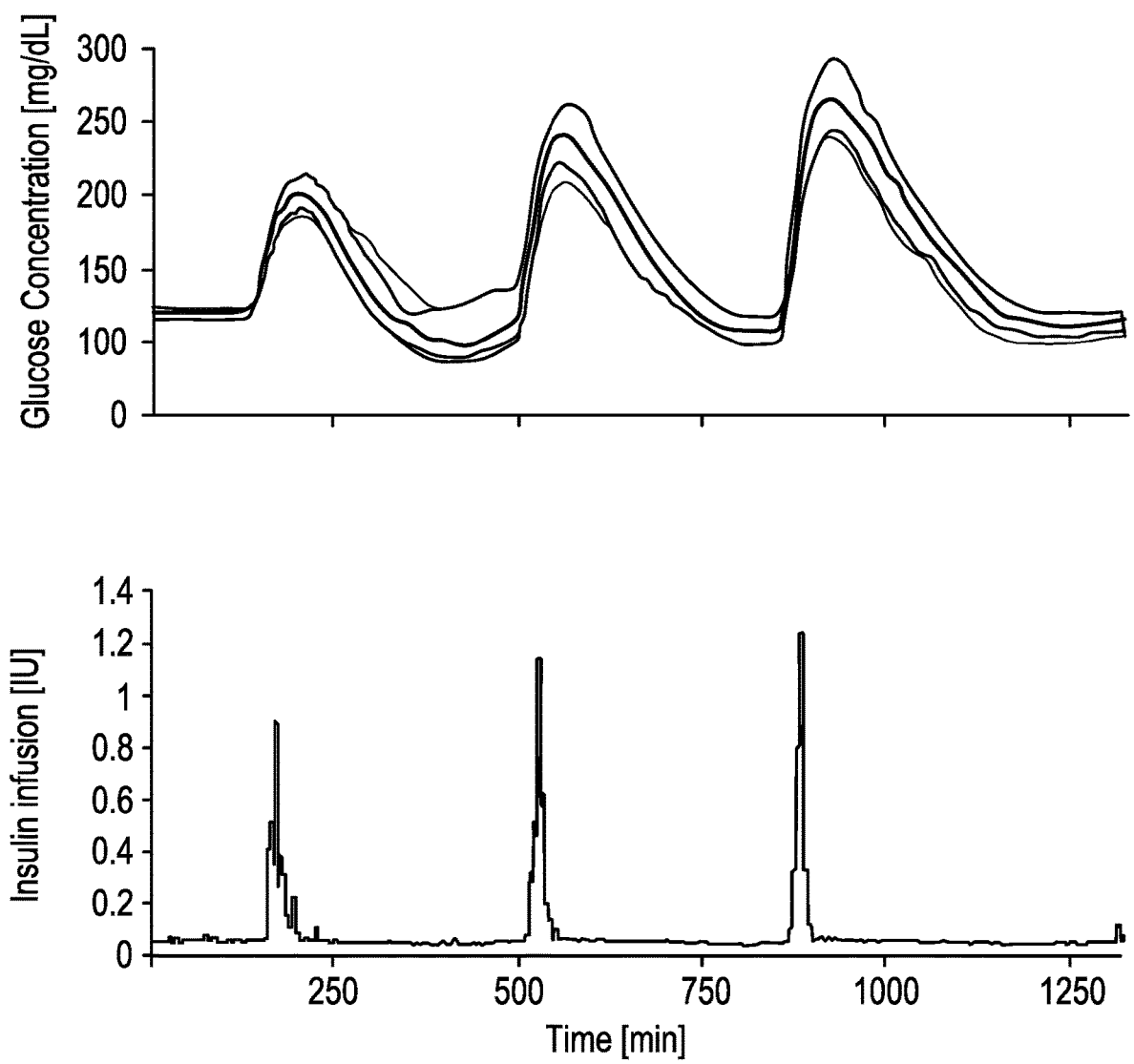
FIG. 9 depicts a chart providing a comparison in median glucose concentration and interquartile range (top) and mean insulin pump administration (bottom) between conservative static tuning (plotted in blue—continuous line) and adaptive tuning (plotted in yellow—discontinuous line) of an MPC controller, the simulated protocol including three unannounced meals compensated using the glucose rate increase detector (GRID) meal detection algorithm, according to an exemplary embodiment.

FIG. 9 depicts a chart providing a comparison in median glucose concentration and interquartile range (top) and mean insulin pump administration (bottom) between conservative static tuning (plotted in blue—continuous line) and adaptive tuning (plotted in yellow—discontinuous line) of an MPC controller, the simulated protocol including three unannounced meals compensated using the glucose rate increase detector (GRID) meal detection algorithm, according to an exemplary embodiment.

In FIG. 9 the same plotting as FIG. 8 is done in a comparison between the conservative and the adaptive controllers. Again, the insulin bolus delivered after the meals is evident for the three unannounced meals, showing very clear spikes shortly after the meal ingestion, as the algorithm takes some time to detect each meal.

The median blood glucose time series shown in the top block of FIG. 8 shows little to no difference in the postprandial period after the first meal of the simulation, which was the smallest of the three (50 g CHO). The same conclusion can be extracted when looking at FIG. 9. Glucose excursions from such a small meal may be countered by the controller independently of the tuning. On the other two meals, clear differences on the median glucose can be observed, being the aggressive glucose lower than the proposed adaptive tuning, and lower than the conservative case. This shows that in the presence of a severe hyperglycemic event, the adaptive controller is allowed to deliver more insulin than the conservative controller. It is also clear, based on the depicted exemplary embodiments, that the adaptive controller delivers this insulin at the safest time, i.e. when the model predictions are accurate, reducing the occurrence of postprandial hypoglycemic events.

Average insulin delivery, shown in the bottom plots of FIGS. 8 and 9, displays no oscillatory behavior for the proposed algorithm or the static tuning scenarios. Average postprandial insulin delivery is lower in the adaptive tuning controller than in the aggressive static case, which explains the lower occurrence of hypoglycemia shown in FIG. 7. As for the conservative versus adaptive case, there seems to be no difference on the average value of insulin delivered at any time of the simulation.

All the meals were not announced to the controller, but a meal detection algorithm based solely on the CGM measurements was implemented, according to the depicted exemplary embodiment. The action taken at the detection of each meal is displayed as large insulin spikes in the bottom plots of FIGS. 8 and 9. The use of a meal detection algorithm influences the performance of the controller when the meals are unannounced as it is reproduced in the simulation results presented above.

Figure 10:
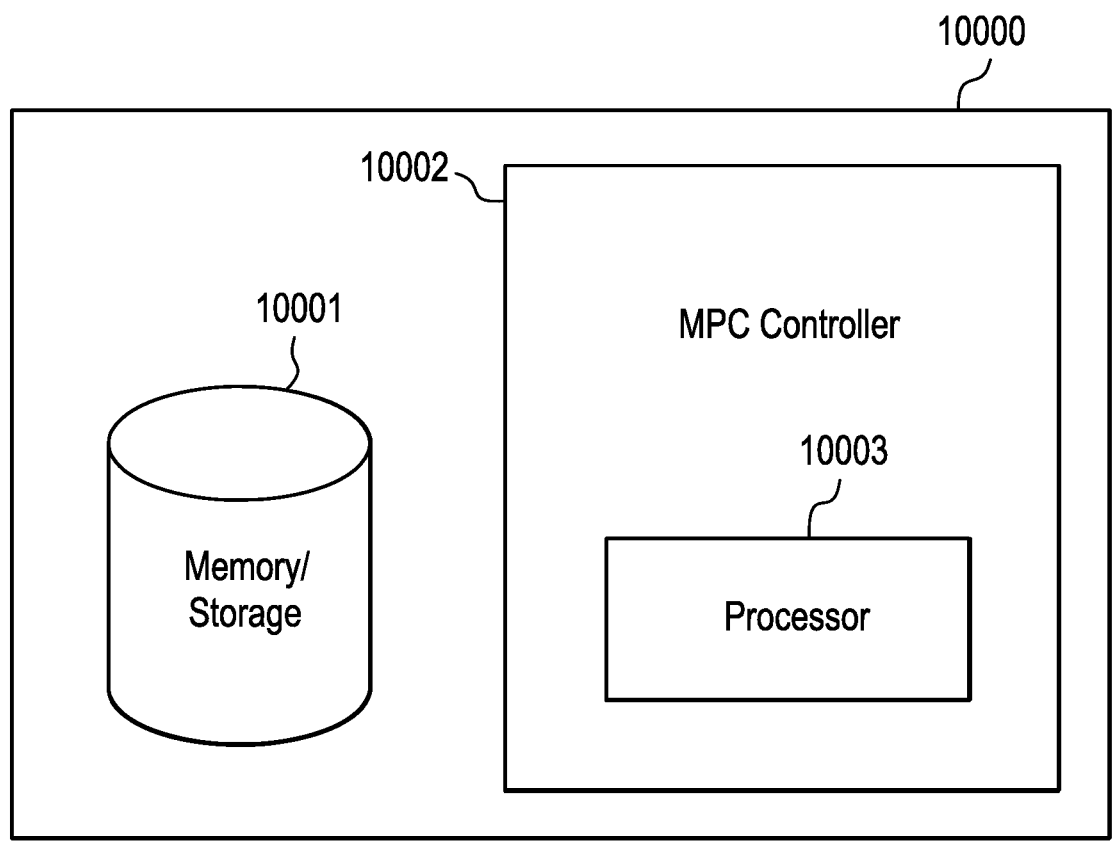
FIG. 10 depicts a block diagram if an apparatus incorporating an MPC controller, according to an exemplary embodiment.

FIG. 10 depicts a block diagram if an apparatus incorporating an MPC controller, according to an exemplary embodiment.

As can be seen in FIG. 10, an exemplary embodiment of an artificial pancreas apparatus 10000 may incorporate a memory/storage 10001, and an MPC controller 10002. The MPC controller may further incorporate a processor 10003. Although a single processor is depicted in FIG. 10, the disclosure is not limited thereto and the MPC controller may incorporate a plurality of processors, according to other exemplary embodiments.

Figure 11:
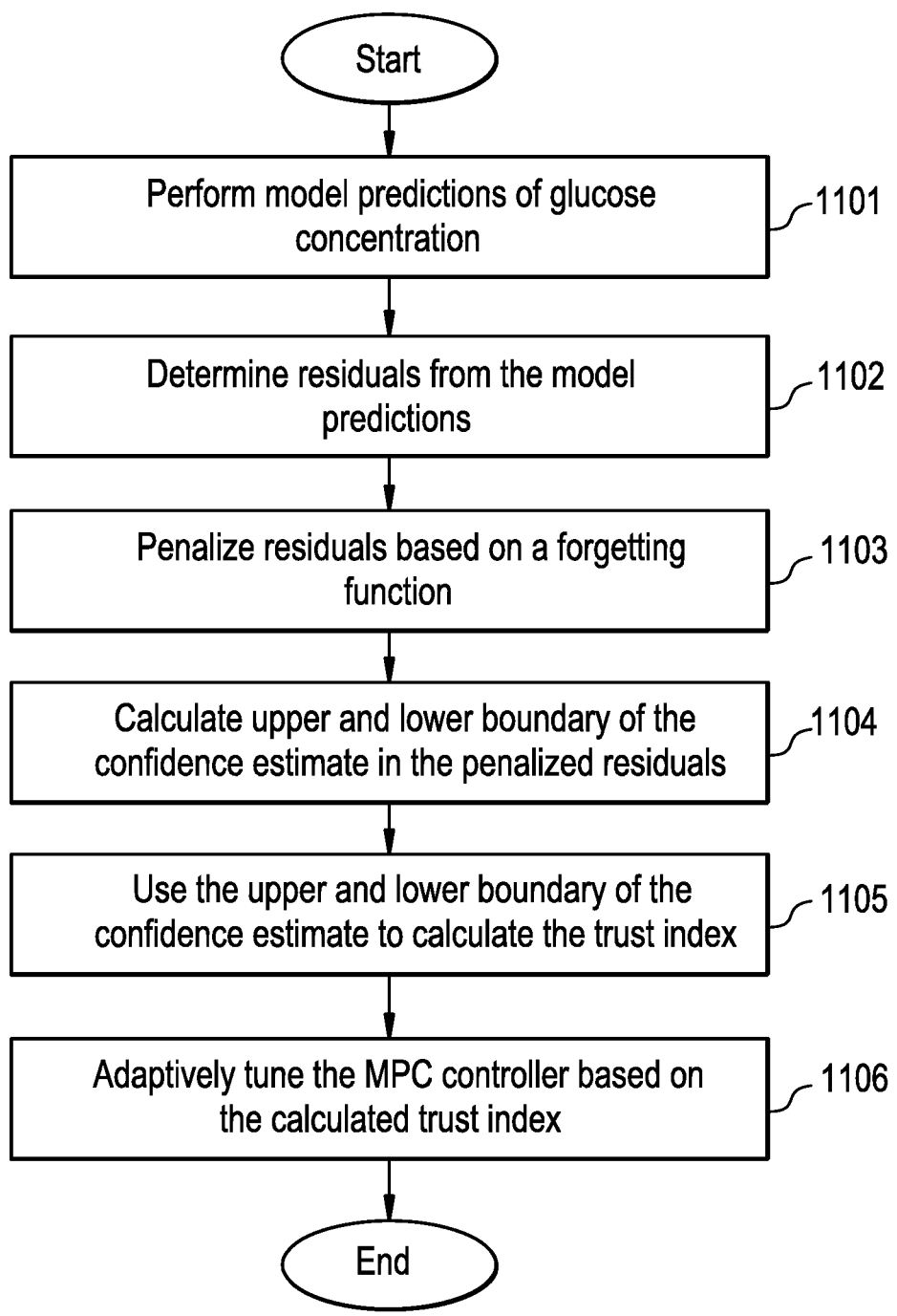
FIG. 11 depicts a flowchart describing the process to adaptively tune an MPC controller, according to an exemplary embodiment.

FIG. 11 depicts a flowchart describing the process to adaptively tune an MPC controller, according to an exemplary embodiment.

The process starts at step 1101 where model predictions are performed on glucose concentrations. Based on the model predictions, residuals are determined in step 1102. The residual may be determined using formula no. 4 recited above, according to an exemplary embodiment.

Further, in step 1103, a forgetting function is used to penalize the residuals in step 1103. The penalized residual may be calculated using formula no. 5 recited above, according to an exemplary embodiment. At step 1104, upper and lower boundary of the confidence estimate in the penalized residuals are calculated. Formulae nos. 6 and 7 can be used for such a calculation according to an exemplary embodiment.

The calculated upper and lower boundary is then used to calculate the trust index in step 1105. The trust index may be calculated using formulae nos. 8 and 9 recited above, according to an exemplary embodiment.

At step 1106, the calculated trust index is used to adaptively tune the MPC controller.

A novel strategy for adaptive tuning of a zone based MPC controller has been described above and its application to a virtual cohort of people with type 1 diabetes. Repeated residuals from the model predictions are stored and a scalar trust index is deduced quantifying the uncertainty of the model predictions and the coherence of the glucose sample at each step, as further detailed using the flowchart of FIG. 11. The MPC controller is then tuned in real time based on the value of the trust index. As can be seen from the simulation comparisons depicted n FIGS. 4-9, the adaptive strategy results in better glucose control than the conservative counterpart, while producing less hypoglycemic episodes and no abnormal insulin delivery profiles were observed upon the application of the adaptive strategy. Delivery of insulin is then controlled based on the adaptively tuned MPC controller.

Figure 12:
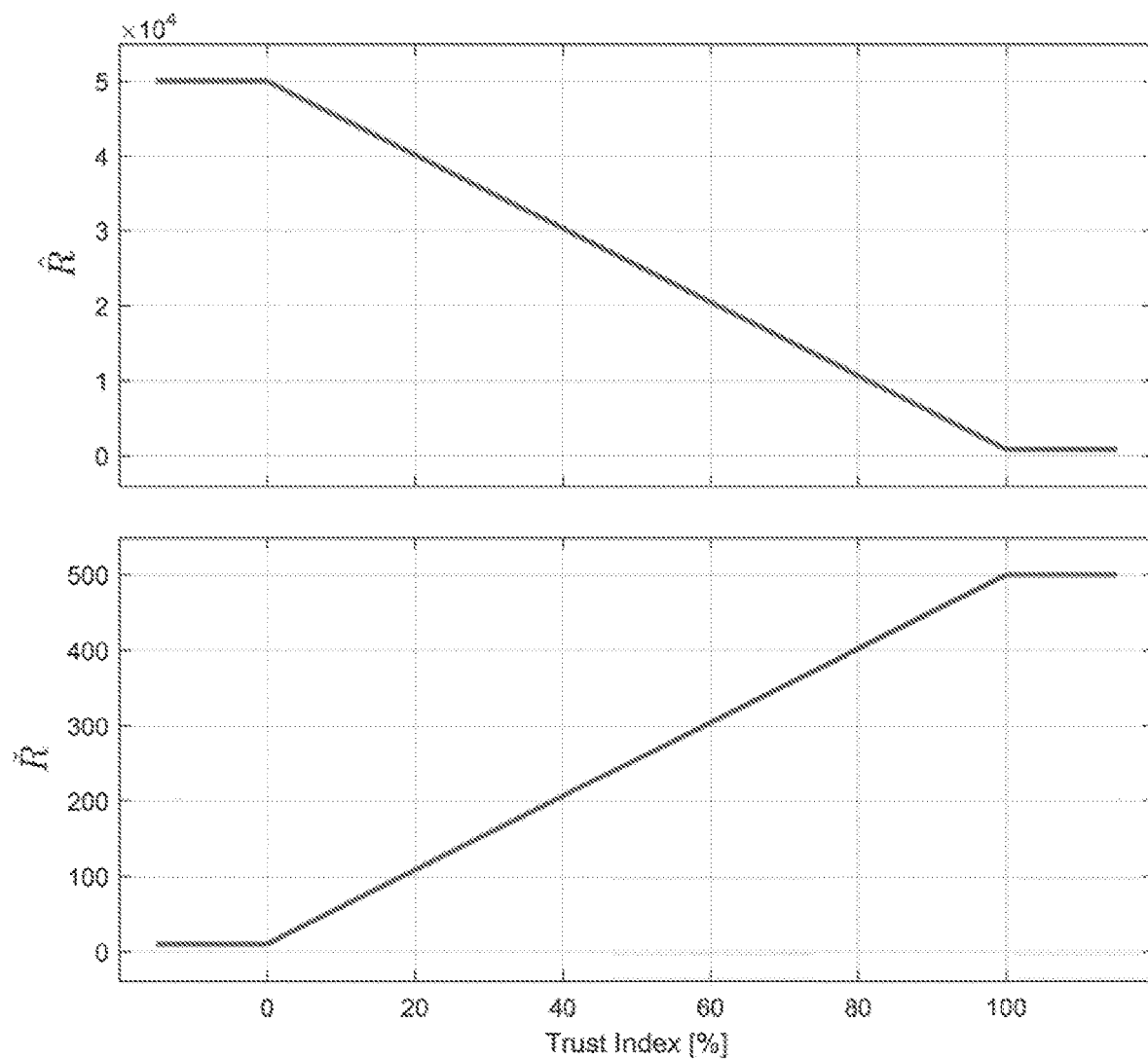
FIG. 12 depicts adaptation scheme for parameters $\hat{R}$ (top) and $\check{R}$ (bottom).

FIG. 12 depicts adaptation scheme for parameters $\hat{R}$ (top) and $\check{R}$ (bottom).

As can be seen, for trust values close to 100% (almost perfect predictions) the parameters assume the aggressive configuration ($\hat{R}$=800, $\check{R}$=500). On the other hand, at a low trust, the parameters are set to the conservative mode ($\hat{R}$=50000, $\check{R}$=10), according to an exemplary embodiment.

FIG. 13 depicts the Mean and standard deviation of the control performance metrics of the zMPC controller for the Default, Aggressive, Conservative, and Adaptive tuning, according to an exemplary embodiment. The performance metrics for the exemplary embodiments described above in the disclosure are depicted in FIG. 13.

"p" values are calculated to show significance between the proposed (adaptive) and other 3 controllers. Values with an asterisk show statistical significance (p<0.05) between the proposed tuning and the default column, as can be seen in FIG. 13.

When comparing strategies GRID and Bolus from FIG. 13, a larger disparity can be observed for the results of each controller configuration for the GRID strategy. This is a direct result of the prandial bolus dosing limiting the amount of insulin that the controller is able to utilize in the post-prandial period, which is one of the safety mechanisms implemented in the controller structure. This yields, for the bolus strategy, more homogeneous results than those of the GRID strategy. As for the GRID strategy results, the adaptive controller produces significantly larger average glucose than the default controller configuration (149 mg/dL vs 147 mg/dL), according to an exemplary embodiment.

However, this difference is clinically irrelevant, with an estimated A1C (based on the average glucose) of 6.81% for the adaptive control and 6.74% for the default controller configuration, according to an exemplary embodiment. The "A1C-average glucose" regression was calculated following: A1C=(avg_glucose+46.7)/28.7. The performance difference is not significant when looking at the time in range (74.6% vs 75% p=0.12), according to an exemplary embodiment. Furthermore, the adaptive scheme is able to significantly reduce the time spent in hypoglycemia, down to 0.16% from the 0.67% of the default controller configuration. The time spent in hypoglycemia for the adaptive scheme is not significantly different than that achieved by the conservative controller configuration. Similarly to what was observed for the bolus strategy experiment, the conservative controller produces a higher average glucose than that of the adaptive control, while also showing a significantly lower time in range. The aggressive controller is able to lower the average glucose more than any of the other configurations, at the cost of much higher frequency of hypoglycemia (1%), according to an exemplary embodiment.

The present disclosure is not limited to the precise construction and compositions disclosed herein; any and all modifications, changes, and variations apparent from the foregoing descriptions are within the spirit and scope of the disclosure as defined in the appended claims. Moreover, the present concepts expressly include any and all combinations and sub combinations of the preceding elements and aspects. An implementation of an apparatus that falls within the inventive concept does not necessarily achieve any of the possible benefits outlined above: such benefits are dependent on the specific use case and specific implementation, and the possible benefits mentioned above are simply examples.

Although the concepts have been described above with respect to the various embodiments, it is noted that there can be a variety of permutations and modifications of the described features by those who are familiar with this field, only some of which have been presented above, without departing from the technical ideas and scope of the features, which is defined by the appended claims.

Further, while this specification contains many features, the features should not be construed as limitations on the scope of the disclosure or the appended claims. Certain features described in the context of separate embodiments can also be implemented in combination. Conversely, various features described in the context of a single embodiment can also be implemented in multiple embodiments separately or in any suitable sub-combination.

Although the drawings describe operations in a specific order and/or show specific arrangements of components, one should not interpret that such specific order and/or arrangements are limited, or that all the operations performed and the components disclosed are needed to obtain a desired result. There are numerous hardware and software devices that can be configured to forward data units in the manner described in the present disclosure with respect to various embodiments. Accordingly, other implementations are within the scope of the following claims.

What is claimed:

1. A method of adaptively tuning a zone based Model Predictive Control (MPC) controller, using at least one processor, the method comprising:
   determining, using at least one of said at least one processor, residuals comprising a difference between:
   glucose values predicted for a current time based on glucose prediction models using previously measured glucose values and glucose values measured at the current time;
   storing, in a memory, the determined residuals;
   penalizing, using at least one of said at least one processor, the determined residuals using a forgetting function, wherein
   the forgetting function is determined using the formula:

$$\widetilde{res}_{k,i}^{t} = res_k^{t-i} \cdot \frac{\log(N_f - i + 1)}{\log N_f} \, \forall \, i \in \mathbb{Z}_1^{N_f}, \forall \, k \in \mathbb{Z}_1^{N_p}$$

where t represents the current time, $res_k^{t-i}$ represents progressively more distant residuals, and $\mathbb{Z}_{k,i}^{t}$ represents the penalized residual;
   calculating a trust index, using at least one of said at least one processor, by quantifying uncertainty of the prediction models using the penalized residuals;
   tuning the MPC controller, in real time, using at least one of said at least one processor, based on the calculated value of the trust index; and determining and delivering an amount of insulin based on the tuning of the MPC controller.

2. The method of claim 1, wherein the determining further comprises determining the residual at time t and for a prediction k steps ahead using the formula:

$$res_k^t = y_{k|t-k} - CGM_t, \forall k \in \mathbb{Z}$$

where $y_{k|t-k}$ represents predicted glucose by the model at time t that was predicted k samples in the past, $N_p$ represents prediction horizon and $CGM_t$ represents current glucose values.

3. The method of claim 2, wherein the storing further comprises storing each of the $N_p$ residuals ($res_k^t$) in a pool of most recent $N_f$ residuals, resulting in a matrix $N_p \times N_f$.

4. The method of claim 1, wherein for each timestamp t each residual is penalized differently.

5. The method of claim 1, wherein the tuning further comprises tuning the MPC conservatively when the determined residuals have a high value or wherein the tuning further comprises tuning the MPC conservatively when the penalized residuals have a high value.

6. The method of claim 1, wherein the tuning further comprises tuning the MPC aggressively when the determined residuals have a low value or wherein the tuning further comprises tuning the MPC aggressively when the penalized residuals have a low value.

7. The method of claim 1, further comprising:
calculating, using at least one of said at least one processor, an estimate of a confidence interval of a current prediction error based on the penalized residuals using the formula:

$$B_x = \max(\text{percentile}_x(\widetilde{res}_k^t), 0) \; \forall k \in \mathbb{Z}_1^{N_p}$$

where $B_k$ is an empirically defined boundary of the confidence interval of a prediction error k steps ahead, and $\text{percentile}_x(\widetilde{res}_k^t)$ represents x-th percentile function of the penalized residual at time t and for a prediction k steps ahead.

8. The method of claim 7, wherein the calculating the estimate of the confidence interval comprises calculating an empirically defined upper boundary $\hat{B}_k$ and an empirically defined lower boundary $\check{B}_k$ using the formula:

$$\hat{B}_k = \max(\text{percentile}_{95}(\widetilde{res}_k^t), 0) \; \forall k \in \mathbb{Z}_1^{N_p}$$

$$\check{B}_k = \min(\text{percentile}_s(\widetilde{res}_k^t), 0) \; \forall k \in \mathbb{Z}^{N_p}$$

9. The method of claim 8, wherein the calculating the trust index comprises calculating the trust index based on the calculated empirically defined upper boundary $\hat{B}_k$ and the calculated empirically defined lower boundary $\check{B}_k$ using the formula:

$$T_t := \hat{B}_k - \check{B}_k + d_H\left(CGM_t, [\check{B} + y_t, \hat{B} + y_t]\right)$$

$$d_H(x, [a, b]) := \begin{cases} 0 & \text{if } x \in [a, b] \\ x - b & \text{if } x > b \\ a - x & \text{if } x < a \end{cases}$$

where $d_H(x, [a, b])$ represents Hausdorff distance from a point x to an interval [a, b], and $y_t$ represents model's prediction of current CGM sample.

10. A method of insulin delivery using an artificial pancreas, the artificial pancreas including at least one processor, the method comprising:
determining, using at least one of said at least one processor, residuals comprising a difference between glucose values predicted at a current time based on glucose prediction models using previously measured glucose values and glucose values measured at the current time;
storing, in a memory, the determined residuals;
penalizing, using at least one of said at least one processor, the determined residuals using a forgetting function, wherein
the forgetting function is determined using the formula:

$$\widetilde{res}_{k,i}^t = res_k^{t-i} \cdot \frac{\log(N_f - i + 1)}{\log N_f} \; \forall i \in \mathbb{Z}_1^{N_f}, \forall k \in \mathbb{Z}_1^{N_p}$$

where t represents the current time, $res_k^{t-i}$ represents progressively more distant residuals, and $\widetilde{res}_{k,i}^t$ represents the penalized residual;
calculating a trust index, using at least one of said at least one processor, by quantifying uncertainty of the prediction models using the penalized residuals;
tuning a model prediction control (MPC) controller, in real time, using at least one of said at least one processor, based on the calculated value of the trust index; and
controlling and delivering, using at least one of said at least one processor, insulin based on the tuned MPC controller.

11. An artificial pancreas apparatus for insulin delivery, the artificial pancreas comprising:
at least one non-transitory memory operable to store program code;
a model prediction control (MPC) controller including at least one processor operable to read said program code and operate as instructed by said program code, said program code causing the at least one processor to:
determine residuals based on prediction models comprising a difference between glucose values predicted at a current time based on glucose prediction models using previously measured glucose values and glucose values measured at the current time;
store, in the at least one non-transitory memory, the determined residuals;
penalize, using at least one of said at least one processor, the determined residuals using a forgetting function, wherein
the forgetting function is determined using the formula:

$$\widetilde{res}_{k,i}^t = res_k^{t-i} \cdot \frac{\log(N_f - i + 1)}{\log N_f} \; \forall i \in \mathbb{Z}_1^{N_f}, \forall k \in \mathbb{Z}_1^{N_p}$$

where t represents current time, $res_k^{t-i}$ represent progressively more distant residuals, and $\widetilde{res}_{k,i}^t$ represents the penalized residual
calculate a trust index by quantifying uncertainty of the prediction models using the penalized residuals; and
tune the MPC controller in real time based on the calculated value of the trust index; and
deliver the insulin based on the tuned MPC controller.

* * * * *